United States Patent [19]

Nishimiya et al.

[11] Patent Number: 5,600,036

[45] Date of Patent: Feb. 4, 1997

[54] 2-TRIFLUOROMETHYL-4-CHLOROBENZALCHLORIDE AND 2-METHYL-3-NITRO-5-CHLOROBENZOTRIFLUORIDE USEFUL AS INTERMEDIATES FOR PREPARING 2-METHYL-3-AMINOBENZOTRIFLUORIDE

[75] Inventors: Takayuki Nishimiya; Masatomi Kanai; Toshikazu Kawai, all of Kawagoe, Japan

[73] Assignee: Central Glass Company, Limited, Yamaguchi, Japan

[21] Appl. No.: 467,678

[22] Filed: Jun. 6, 1995

Related U.S. Application Data

[62] Division of Ser. No. 177,490, Jan. 5, 1994, Pat. No. 5,449,831.

[30] Foreign Application Priority Data

Jan. 18, 1993 [JP] Japan .......................... 5-6184

[51] Int. Cl.$^6$ .................................................. C07C 205/06
[52] U.S. Cl. ........................... 568/937; 570/124; 570/144
[58] Field of Search ........................... 562/840; 568/937; 570/124, 144

[56] References Cited

U.S. PATENT DOCUMENTS

| | | | |
|---|---|---|---|
| 3,839,344 | 10/1974 | Sherlock | 260/295.5 R |
| 3,891,761 | 6/1975 | Sherlock | 424/266 |
| 4,132,737 | 1/1979 | Molloy | 260/578 |
| 4,209,464 | 6/1980 | Steinman et al. | 260/578 |
| 4,503,276 | 3/1985 | Nickson | 568/936 |
| 4,749,813 | 6/1988 | Marhold et al. | 564/442 |
| 4,831,193 | 5/1989 | Lamendola et al. | 564/417 |

FOREIGN PATENT DOCUMENTS

| | | |
|---|---|---|
| 0295674 | 12/1988 | European Pat. Off. . |
| 2194533 | 3/1988 | United Kingdom . |

OTHER PUBLICATIONS

CA 73:87890u (Oct. 26, 1970).
CA 103:12316f (Oct. 14, 1985).

*Primary Examiner*—Brian M. Burn
*Attorney, Agent, or Firm*—Keck, Mahin & Cate

[57] ABSTRACT

2-Trifluoromethyl-4-chloro-benzalchloride and 2-methyl-3-nitro-5-chlorobenzotrifluoride, are intermediates in a process of preparing 2-methyl-3-aminobenzo-trifluoride. In this process, 2-trifluoromethyl-4-chlorobenzal-chloride is prepared by chlorinating o-trifluoromethylbenzalhalide, and 2-methyl-3-nitro-5-chlorobenzotrifluoride is prepared at first by hydrogenating the 2-trifluoro-methyl-4-chlorobenzalhalide to form a 2-methyl-5-monochlorobenzotrifluoride and then by nitrating the 2-methyl-5-monochlorobenzotrifluoride. Following this process, 2-methyl-3-aminobenzotrifluoride (MA-BTF) is prepared by hydrogenating the 2-methyl-3-nitro-5-chlorobenzotrifluoride. The thus prepared 2-methyl-3-aminobenzotrifluoride is useful as an intermediate in preparing medicines, agricultural chemicals and other chemical products.

2 Claims, No Drawings

2-TRIFLUOROMETHYL-4-CHLOROBENZALCHLORIDE AND 2-METHYL-3-NITRO-5-CHLOROBENZOTRIFLUORIDE USEFUL AS INTERMEDIATES FOR PREPARING 2-METHYL-3-AMINOBENZOTRIFLUORIDE

This is a Rule 60 divisional of application Ser. No. 08/177,490, filed Jan. 5, 1994 now U.S. Pat. No. 5,449,831.

BACKGROUND OF THE INVENTION

The present invention relates to a novel process of preparing a 2-methyl-3-aminobenzotrifluoride (MA-BTF) which is useful as an intermediate of some medicines, agricultural chemicals and other chemical products. For example, U.S. Pat. Nos. 3,891,761 and 3,839,344 disclose the N-methyl-D-glucamine salt of 2-(2'-methyl-3'-trifluoromethylanilino) nicotinic acid which is derived from MA-BTF and particularly suitable as a parenterally administered analgesic agent.

There have been some proposals of process for preparing MA-BTF. For example, U.S. Pat. No. 4,209,464 discloses a process of preparing MA-BTF from 3-amino-4-chlorobenzotrifluoride. In this method, at first, 3-amino-4-chlorobenzotrifluoride is reacted with dimethylsulfoxide in the presence of phosphorus pentoxide and triethylamine to produce N-(2-chloro-5-trifluoromethyl) phenyl-S,S-dimethylsulfimide. Then, the dimethylsulfimide is converted to 3-amino-4-chloro-2-methylthiomethylbenzotrifluoride by a chemical rearrangement. Then, this trifluoride is reduced with Raney nickel to form MA-BTF. However, in this process, due to the use of a large amount of phosphorus pentoxide, there are some problems in the recovery method and the processing method of the product. Therefore, this process is not suitable for operation in an industrial scale.

GB-B-2194533 discloses another process of preparing MA-BTF. In this process, at first, 3,4-dichlorotoluene is converted to 2-methyl-4,5-dichlorobenzotrichloride by carbon tetrachloride in the presence of aluminum chloride. Then, this trichloride is fluorinated to form 2-methyl-4,5-dichlorobenzotrifluoride. Then, this trifluoride is nitrated to form 2-methyl-3-nitro-4,5-dichlorobenzotrifluoride. Then, this trifluoride is hydrogenated to form MA-BTF. However, this process is not recommendable from an environmental point of view because carbon tetrachloride which is considered to destroy the ozone layer of the earth is used as a raw material.

SUMMARY OF THE INVENTION

It is therefore an object of the present invention to provide a novel process of preparing MA-BTF, which is free from the above-mentioned drawbacks.

According to the present invention, there is provided a process of preparing a 2-methyl-3-aminobenzotrifluoride, comprising the steps of:

(a) halogenating o-trifluoromethylbenzalhalide to form a 2-trifluoromethyl-4-halogenobenzalhalide;

(b) hydrogenating said 2-trifluoromethyl-4-halogenobenzalhalide to form a 2-methylmonohalogenobenzotrifluoride;

(c) nitrating said 2-methylmonohalogenobenzotrifluoride to form a 2-methyl-3-nitro-5-halogenobenzotrifluoride; and (d) hydrogenating said 2-methyl-3-nitro-5-halogenobenzotrifluoride to form said 2-methyl-3-aminobenzotrifluoride.

By a process according to the present invention, MA-BTF can be produced with high yields and high productivity through 2-trifluoromethyl-4-chlorobenzalchloride and 2-methyl-3-nitro-5-chlorobenzotrifluoride which are novel compounds without using a process which is industrially hard to be conducted and without using a raw material which would be possibly prohibited to be used.

DESCRIPTION OF THE PREFERRED EMBODIMENTS

A process according to the present invention for preparing MA-BTF comprises first, second, third and fourth steps as follows:

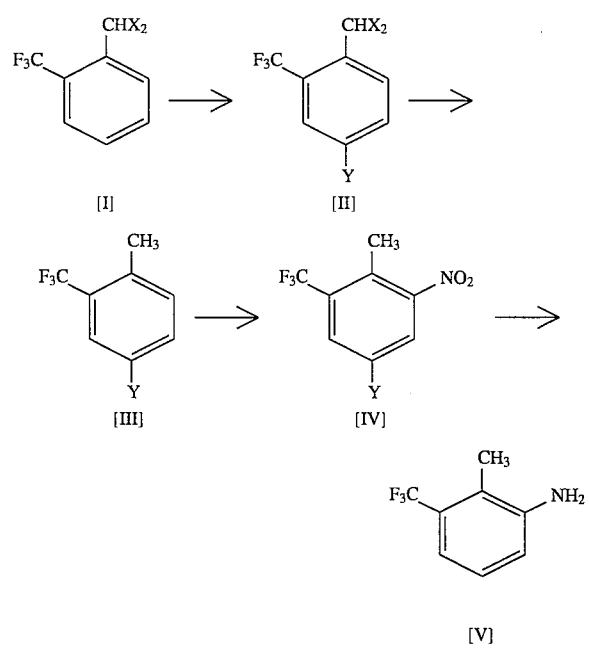

wherein X and Y are the same or different halogen atoms and selected from the group consisting of Cl, Br and I.

The first step of the process is a mono-halogenation reaction in which o-trifluoromethylbenzalhalide [I] is brought into contact with a halogen in the presence of a catalyst. The reaction liquid after the first step is washed with water. The product of the first step is a mixture of nuclear mono-halogenated compounds in which a main product is 2-trifluoromethyl-4-halogenobenzalhalide [II]. Examples of o-trifluoromethylbenzalhalide [I] are o-trifluoromethylbenzalchloride, o-trifluoromethylbenzabromide and o-trifluoromethylbenzaliodide. In an industrial operation of the first step, the most preferable combination of o-trifluoromethylbenzalhalide and the halogen are o-trifluoromethylbenzalchloride and chlorine, respectively. Preferable examples of the catalyst in the first step are ferric chloride, ferric bromide, aluminum chloride, aluminum bromide and antimony pentachloride. It is optional to add a promoter such as iodine. It is preferable that the reaction temperature of the first step is from 60° to 100° C. If it is lower than 60° C., the reaction proceeds too slowly. If it is higher than 100° C., the production of poly-halogenated compound(s) undesirably increases.

The second step of the process is a dehalogenation reaction to remove halogens bonded to the benzal group of 2-trifluoromethyl-4-halogenobenzalhalide [II]. In the second step, the mono-halogenated compounds obtained by the first step are brought into contact with hydrogen under a liquid phase condition in the presence of a metal-carried catalyst and an optional basic substance. After the dehalogenation reaction, the catalyst and the salt are removed by filtration. Then, the filtrate is washed with water and then dried with a drying agent. Then, the drying agent is removed by filtration. The product of the second step is a mixture of 2-methylmonohalogenobenzotrifluoride in which a main product is 2-methyl-5-halogenobenzotrifluoride [III].

The reaction temperature of the second step is preferably from 0° to 100° C. If it is lower than 0° C., the reaction becomes too slow. If it is higher than 100° C., hydrogenation of the nuclear halogen undesirably occurs by super-hydrogenation.

In the third step of the process, 2-methylmonohalogenobenzotrifluoride obtained by the second step is nitrated by nitric acid in the presence of sulfuric acid. Then, the resultant solution is separated into two phases, and the organic phase is washed with water, then with a basic solution and then with water. The product of the third step is a mixture of nitrated compounds in which a main product is 2-methyl-B-nitro-5-halogenobenzotrifluoride [IV].

It is preferable to use concentrated sulfuric acid, fuming sulfuric acid or anhydrous sulfuric acid as the sulfuric acid used in the third step. The reaction temperature of the third step is preferably from 0° to 80° C. If it is lower than 0° C., the reaction speed becomes too slow. If it is higher than 80° C., undesirable polynitration occurs. It is optional to conduct the reaction of the third step in an inactive organic solvent such as methylene chloride, chloroform, dichloroethane or trichloroethane.

In the fourth step of the process, the nitrated compounds obtained by the third step are brought into contact with hydrogen under a liquid phase condition in the presence of a metal-carried catalyst and an optional basic substance so as to reduce the nitro group of the nitrated compounds and to dehalogenate the nitrated compounds. After the reaction, the catalyst and the salt are removed by filtration. Then, the filtrate is washed with water and then dried with a drying agent. Then, the drying agent is removed by filtration. The product of the fourth step is a mixture of isomers in which a main product is MA-BTF. Only MA-BTF is isolated by recrystallization, crystallization or distillation after the fourth step.

The reaction temperature of the fourth step is preferably from 60° to 130° C. If it is lower than 60° C., the reaction becomes too slow. If it is higher than 130° C., hydrogenation of the trifluoromethyl group undesirably occurs by super-hydrogenation.

The metal-carried catalyst of the second and fourth steps has a metal such as a noble metal (for example, Pd, Pt or Rh) or nickel which is carried by a carrier such as active carbon, alumina, zeolite or silica-alumina. Preferred examples of the metal-carried catalyst of the second and forth steps are a combination of Pd and active carbon (Pd/carbon), a combination of Pd and alumina (Pd/alumina), a combination of Pd and zeolite (Pd/zeolite) and a combination of Pd and silica-alumina (Pd/silica-alumina). It is preferable that the amount of the metal-carried catalyst of the second and fourth steps is from 0.1 to 5.0 wt % of the substrate. If it is less than 0.1 wt %, the reaction becomes too slow. There is no strict umber limit to the amount of the metal-carried catalyst. However, it is not necessary to add the same which is more than 5.0 wt %. The amount of the metal of the catalyst is from 0.1 to 10 wt %. A commercial metal-carried catalyst containing 0.5–5.0 wt % metal can be used in the second and fourth steps.

The optional basic substance of the second and fourth steps is a hydroxide of an alkali metal or of an alkali earth metal, a carbonate of an alkali metal or of an alkali earth metal, an acetate of an alkali metal or of an alkali earth metal, a borate of an alkali metal or an alkali earth metal, or a phosphate of an alkali metal or an alkali earth metal. Preferable examples of the basic substance used in the second and forth steps are sodium hydroxide, potassium hydroxide, calcium hydroxide, sodium carbonate, potassium carbonate, sodium acetate, potassium acetate, sodium borate, potassium borate, disodium phosphate and trisodium phosphate.

The pressure of hydrogen in the second and fourth steps is preferably from 1 to 20 kg/cm$^2$. If it is lower than 1 kg/cm$^2$, the reaction speed becomes too slow. If it is higher than 20 kg/cm$^2$, the reaction proceeds satisfactorily. However, the pressure higher than 20 kg/cm$^2$ is not preferable because apparatus becomes limited in terms of structure.

The reactions of the second and fourth steps are gas-liquid reactions. Therefore, contact efficiency between the gas and the liquid influences the reaction speed significantly. Thus, it is preferable to use a special apparatus designed to improve contact efficiency, for example, by a sufficient stir. The reactions of the second and fourth steps can be conducted in water or an inactive organic solvent such as diethyl ether, methanol, ethanol or isopropanol.

In the present invention, the main product of each step of the process may be concentrated or isolated through distillation, recrystallization or crystallization.

The present invention is further illustrated by the following nonlimitative example.

EXAMPLE

MA-BTF was produced by a process comprising the following first, second, third and fourth steps.

First Step (Production of 2-trifluoromethyl-4-chlorobenzalchloride)

A 500-ml four-necked round bottom flask equipped with thermometer, mechanical stirrer, Dimroth condenser and chlorine-introducing tube was charged with 570.0 g (2.5 mol) of o-trifluoromethylbenzalchloride, 11.5 g (2.5 mol %) of ferric chloride and 1.5 g (0.5 mol %) of iodine. Then, the reaction temperature was raised to 60° C. while the mixture was kept stirred. When the reaction temperature reached 60° C., chlorination was started by continuously introducing chlorine at a rate of 0.5 mol/hr. After the lapse of 2 hr, the reaction temperature was raised to 80° C., and then the reaction was continued for another 5 hr. After the 7-hr reaction, conversion was 97.0%. Then, the reaction liquid was put into a 1000-ml separating funnel, and washed two times with 500 ml of water. The mixed liquid was allowed to separate into two layers and the aqueous layer was removed. The organic phase was dried with magnesium sulfate, and then magnesium sulfate was removed by vacuum filtration. As the result, 634.2 g of 2-trifluoromethyl-4-chlorobenzalchloride (purity: 72.1%) was obtained. The yield of this product was 69.4%. The product was analyzed by gas chromatography, and the result is as follows.

bp: 86°–88° C. (4–5 mmHg)

MASS: m/z 262 (M+)

227 (M+—Cl)

192 (M+—Cl—Cl)

177 (M+—Cl—CF$_3$)
157 (M+—Cl—Cl—Cl)
NMR: (1H in CDCl$_3$, TMS) δ7.02 ppm (S, 1H) 7.57–8.12 ppm (m, 3H)
($^{19}$F in CFCl$_3$, TMS) –59.34 ppm (S, 3F)

Second Step (Production of 2-methyl-5-chlorobenzotrifluoride)

A 1000-ml autoclave which is equipped with a mechanical stirrer and made of stainless steel (SUS-316) was charged with 263.6 g (1.0 mol) of the isomeric mixture (the product of the first step) containing 0.72 mol of 2-trifluoromethyl-4-chlorobenzalchloride as a main component, 84 g (2.1 mol) of sodium hydroxide and 420 g of water. Then, 5.3 g (2.0 wt %) of a metal-carried catalyst (5%-Pd/carbon) was added to the autoclave. The atmosphere of the autoclave was replaced by hydrogen, and the autoclave was put into oil bath to increase the temperature to 30° C. At the same time, stir was started while the hydrogen pressure was maintained at 5 kg/cm$^2$. This started absorption of hydrogen. After the lapse of 4 hr, stir was stopped, and the reaction liquid was allowed to cool down. By analysis, conversion of 2-trifluoromethyl-4-chlorobenzalchloride (purity: 72.1%) was 99.9%. Then, the catalyst and the salt were removed by vacuum filtration. The resultant solution was put into a 1000-ml separating funnel, and then the aqueous phase was removed. The organic phase was washed with 500 ml of water and dried with magnesium sulfate. Then, magnesium sulfate was removed by vacuum filtration. As the result, 171.6 g of 2-methyl-5-chlorobenzotrifluoride (purity: 63.8%) was obtained. The yield of this product was 79.0%.

Third step (Production of 2-methyl-3-nitro-5-chlorobenzotrifluoride)

A 300-ml four-necked round bottom flask equipped with thermometer, mechanical stirrer, Dimroth condenser and 200-ml dropping funnel was charged with 144.4 g (0.75 mol) of an isomeric mixture (the product of the second step) containing 0.48 mol of 2-methyl-5-chlorobenzotrifluoride as a main component. Separately, an acid mixture was prepared by mixing 52.0 g (0.83 mol) of fuming nitric acid and 220.5 g (2.25 mol) of concentrated sulfuric acid. The total amount of the acid mixture was added by dropping to the flask by spending 1 hr while the reaction liquid was kept stirred and the reaction temperature was maintained at a temperature ranging from 20° to 30° C. After the addition of the acid mixture, the reaction was continued for 3 hr while the reaction temperature was maintained at a temperature ranging from 20° to 30 ° C. Then, stir was stopped. By analysis, conversion was 99.8%, and the purity of 2-methyl-3-nitro-5-chlorobenzotrifluoride was 52.2%. After the reaction, the resultant solution was put into a 1000 ml separating funnel, and the acid mixture phase was removed. Then, the organic phase was washed with 500 ml of water, and then dried with magnesium sulfate. Then, magnesium sulfate was removed by vacuum filtration. As the result, 97.2 g of 2-methyl-3-nitro-5-chlorobenzotrifluoride (purity: 89.0%, boiling point: 119°–125° C. at 21–26 mmHg) was obtained by the concentration through vacuum distillation. The yield was 75.9%. The product was analyzed by gas chromatography, and the result is as follows.

bp: 119°–122° C. (21–23 mmHg)
MASS: m/z
239 (M+)
222 (M+—O–H)
194 (M+—CH$_3$–NO)
NMR: (1H in CDCl$_3$, TMS)δ2.53 ppm (S, 3H) 7.57–7.91 ppm (m, 2H)
($^{19}$F in CFCl$_3$, TMS) –61.56 ppm (S, 3F)

Fourth step (Production of MA-BTF)

A 500-ml autoclave which is equipped with a mechanical stirrer and made of stainless steel (SUS-316) was charged with 71.1 g (0.3 mol) of the isomeric mixture (the product of the third step) containing 0.27 mol of 2-methyl-3-nitro-5-chlorobenzotrifluoride as a main component, 13.2 g (0.33 mol) of sodium hydroxide and 100 g of water. Then, 1.4 g (2.0 wt %) of a metal-carried catalyst (5%-Pd/carbon) was added to the autoclave. The atmosphere of the autoclave was replaced by hydrogen, and the autoclave was put into oil bath to increase the temperature to 80° C. At the same time, stir was started while the hydrogen pressure was maintained at 5 kg/cm$^2$. This started absorption of hydrogen. After the lapse of 4 hr, stir was stopped, and the reaction liquid was allowed to cool down. By analysis, conversion of 2-methyl-3-nitro-5-chlorobenzotrifluoride was 99.9%. Then, the catalyst and the salt were removed by vacuum filtration. The resultant solution was put into a 1000-ml separating funnel, and then the aqueous phase was removed. The organic phase was washed with 500 ml of water and dried with magnesium sulfate. Then, magnesium sulfate was removed by vacuum filtration. As the result, 44.3 g of MA-BTF (purity: 94.4%) was obtained. The yield of MA-BTF was 88.5%. This product was put into a 200 ml beaker, and then 100 ml of n-hexane was put into the beaker. The liquid temperature was lowered to –10° C. so as to recrystallize MA-BTF while the mixture was kept stirred. The recrystallized product (purity: 99.5%) was isolated by filtration. The solvent remaining in the recrystallized product was removed by evaporation. As the result, 34.3 g of the purified product (MA-BTF) was obtained. The yield was 72.6% (yield in recrystallization: 82.0%).

What is claimed is:

1. 2-Trifluoromethyl-4-chlorobenzalchloride prepared by chlorinating o-trifluoromethylbenzalhalide.

2. 2-Methyl-3-nitro-5-chlorobenzotrifluoride prepared by a process comprising the steps of:

(a) chlorinating o-trifluoromethylbenzalhalide to form a 2-trifluoromethyl-4-chlorobenzalhalide;

(b) hydrogenating said 2-trifluoromethyl-4-chlorobenzalhalide to form a 2-methyl-5-monochlorobenzotrifluoride; and (c) nitrating said 2-methyl-5-monochlorobenzotrifluoride to form said 2-methyl-3-nitro-5-chlorobenzotrifluoride.

* * * * *